US00PP29467P3

(12) United States Plant Patent
Bédard

(10) Patent No.: US PP29,467 P3
(45) Date of Patent: Jul. 10, 2018

(54) FLORIBUNDA ROSE PLANT NAMED 'WEKFAWIBYBLU'

(50) Latin Name: *Rosa hybrida*
Varietal Denomination: WEKfawibyblu

(71) Applicant: Early Morning LLC, Lawrenceburg, IN (US)

(72) Inventor: Christian Bédard, Placentia, CA (US)

(73) Assignee: Early Morning, LLC, Pomona, CA (US)

( * ) Notice: Subject to any disclaimer, the term of this patent is extended or adjusted under 35 U.S.C. 154(b) by 0 days.

(21) Appl. No.: 15/530,047

(22) Filed: Nov. 23, 2016

(65) Prior Publication Data

US 2018/0146584 P1 May 24, 2018

(51) Int. Cl.
*A01H 5/02* (2018.01)

(52) U.S. Cl.
USPC ..... Plt./149

(58) Field of Classification Search
USPC ..... Plt./141, 149
See application file for complete search history.

(56) References Cited

U.S. PATENT DOCUMENTS

PP12,645 P2 5/2002 Weatherly
PP20,325 P3 9/2009 James

OTHER PUBLICATIONS

Weeks Roses, 2017 Catalog, 92 pages.

*Primary Examiner* — Susan McCormick Ewoldt
(74) *Attorney, Agent, or Firm* — McKee, Voorhees & Sease, PLC

(57) ABSTRACT

A new variety of Floribunda rose suitable for garden decoration, having flowers of fuchsia pink with lighter reverse coloration.

1 Drawing Sheet

Classification: The present invention relates to a new *Rosa hybrida* plant.

Variety denomination: The new plant has the varietal denomination 'WEKfawibyblu'.

BACKGROUND OF THE INVENTION

This invention relates to a new and distinct variety of Floribunda Rose. It has a non-disseminated seedling of my creation as its seed parent with the following genetic origin (seedling X Wild Blue Yonder) and as its pollen parent the variety known as 'PEJamblu' (U.S. Plant Pat. No. 20,325).

SUMMARY OF THE INVENTION

Among the features which distinguish the new variety from other presently available and commercial rose cultivars known to the inventor are the following combinations of characteristics: its abundant blooms, its moderate clove with hints of cinnamon fragrance, its large clusters with multiple flowers and its several small prickles on the branches and new shoots. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKfawibyblu' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKfawibyblu' bears double flowers (about 20 to 30 petals) of fuchsia pink with lighter reverse coloration, the non-disseminated seedling bears very double flowers of lavender coloration with significantly heavier petalage (about 35 to 52 petals). The new variety has an upright moderately spreading medium height growing habit (about 130 to about 180 cm. in height), whereas the seed parent has a rounded bushy significantly shorter growing habit (about 100 to about 120 cm. in height).

The new variety may be distinguished from its pollen parent, 'PEJamblu' by the following combination of characteristics: whereas 'WEKfawibyblu' bears double flowers (about 20 to 30 petals) of fuchsia pink with lighter reverse coloration, 'PEJamblu' bears semi-double flowers of mauve-lilac ageing to slate blue coloration with significantly lesser petalage (about 12 to 16 petals). The new variety has a moderate clove with hints of cinnamon fragrance, whereas the pollen parent has a very strong citrus fragrance.

COMPARISON WITH THE CLOSEST COMMERCIALLY AVAILABLE CULTIVAR

The new variety may be distinguished from its closest commercially available cultivar, 'PRObril' (U.S. Plant Pat. No. 12,645) by the following combination of characteristics: whereas 'WEKfawibyblu' bears double flowers (about 20 to 30 petals) of fuchsia pink with lighter reverse coloration, 'PRObril' bears double flowers of deep pink and cream coloration with heavier petalage (about 27 to 32 petals). The new variety has an upright moderately spreading medium height growing habit (about 130 to about 180 cm. in height), whereas the closest commercially available cultivar has a bushy upright significantly shorter growing habit (about 75 to about 90 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, usually in clusters of two to twenty-eight or more per stem. Flowers may be borne in rounded clusters on strong medium to somewhat long length stems (about 18 to about 115 cm.). The cluster ranges from about 9.2 to about 27.5 cm. in diameter. Outdoors, the plant blooms abundantly and nearly continuously during the growing season. The flowers have a moderate clove with hints of cinnamon fragrance.

BUD

The peduncle is about 2.3 to about 4.1 cm. in length, of average caliper (about 0.2 to about 0.3 cm. in diameter), and usually erect to somewhat stiff. It is moderately rough, with some stipitate glands, few hairs and occasionally few small prickles. Peduncle color is between 144A and 146B sometimes moderately suffused, especially on the side exposed to the sun, with between 187C and 187D.

Before the calyx breaks, the bud is about 0.9 to about 1.5 cm. in diameter at the widest point, about 1.2 to about 2.0 cm. in length, and pointed to somewhat ovoid in shape. The surface of the bud bears between 4 to 6 foliaceous appendages, some stipitate glands and hairs, usually with slender entire foliaceous parts extending beyond the tip of the bud about ¼ or more of its length. Bud color is between 146B and 137D sometimes moderately suffused, especially on the side exposed to the sun, with between 187B and 187A.

The sepals are about 1.9 to about 2.8 cm. in length and about 0.7 to about 1.0 cm. in width at the widest point. The outer surface color of the sepal is between 146B and 137D sometimes moderately suffused, especially on the side exposed to the sun, with between 187B and 187A. The outer surface of the sepal is moderately rough and bears between 0 to 3 foliaceous appendages with some stipitate glands and hairs. The inner surface color of the sepal is near 146D broadly bordered by near 138A. After the sepals open, the inner surface color is sometimes moderately suffused, especially on the area exposed to the sun, with between 187B and 187A. The inner surface of the sepal is covered with fine wooly tomentum; sepal margins are lined with some stipitate glands and hairs.

The receptacle of the flower is of moderately long length (about 0.6 to about 0.8 cm.) and average to somewhat heavy in caliper (about 0.6 to about 0.8 cm. in diameter). The receptacle is urn-shaped in form. Its surface is smooth with few hairs and with thin fleshy walls. The receptacle color is between 137C and 137D.

As the petals open (after the calyx breaks), the bud is about 1.4 to about 2.2 cm. in diameter at the widest point, about 1.6 to about 2.9 cm. in length, and moderately globular to somewhat ovoid in form. The color of the under surfaces of the newly opened petals is between 159D and 158C moderately suffused with between 60C and 64B to as dark as between 61A and 60B mostly toward the edge of the petal, sometimes moderately streaked with near 187B in the middle of the petal. At the point where the petal attaches, there is a large zone of between 154D and 1D. The color of the upper surfaces of the newly opened petals is between 60B and 60C often moderately suffused with between 187B and 187A. At the point where the petal attaches, there is a large zone of between 154D and 1D.

BLOOM

When fully open, the bloom ranges from about 6.4 to about 10.4 cm. in diameter. Petalage is double with about 20 to 30 petals and about 3 to 10 petaloids irregularly arranged. When partially open, the bloom form is moderately ovoid to somewhat high centered to cupped, and the petals are loosely spiraled to cupped to somewhat undulated with petal edges somewhat reflexed outward. When fully open, the bloom form is more cupped, and the petals are loosely cupped to somewhat undulated with petal edges somewhat reflexed outward.

PETALS

The substance of the petals is moderately heavy and of somewhat thin to medium thickness, with upper surfaces moderately satiny and under surfaces slightly shiny to almost matte. The petals are about 3.5 to about 5.2 cm. in length and about 2.5 to about 4.6 cm. in width at the widest point. Petal margins are entire.

The outer petals are broadly obovate in shape with rounded apices.

The inner petals are moderately obovate to somewhat oblanceolate in shape with rounded apices.

Petaloids are about 1.4 to about 4.0 cm. in length and about 0.8 to about 2.5 cm. in width at the widest point. Petaloids are irregularly shaped somewhat obovate to moderately oblanceolate with rounded apices.

NEWLY OPENED FLOWER

The under surface color of the outer petals is between 158D and 155A lightly suffused with between 71C and 71D. There is no visible change in coloration at the point where the petal attaches. The upper surface color of the outer petals is between 74A and 74B. At the point where the petal attaches, there is a large zone of between 158D and 155A.

The under surface color of the intermediate and inner petals is between 158D and 155A lightly suffused with between 67B and 71D. The upper surface color of the intermediate and inner petals is between 67B and 66B.

The under and upper surface colors of the petaloids are similar in coloration to the upper and under surfaces of the intermediate and inner petals.

The general tonality of the newly opened flower is between 67B and 66B.

THREE-DAY-OLD FLOWER

The under surface color of the outer petals is between 155B and 155A lightly suffused with between 78A and 74B. There is no visible change in coloration at the point where the petal attaches. The upper surface color of the outer petals is between 78A and 74B sometimes lightly suffused with near 77A. At the point where the petal attaches, there is a large zone of between 155B and 155A.

The under surface color of the intermediate and inner petals is between 155B and 155A lightly suffused with near 73A. The upper surface color of the intermediate and inner petals is between 72D and 73A.

The under and upper surface colors of the petaloids are similar in coloration to the upper and under surfaces of the intermediate and inner petals.

The general tonality of the three-day-old flower is between 72D and 73A.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 80) and are arranged regularly about the pistils; a few are mixed with petaloids. The filaments are of medium to somewhat long length (about 0.5 to about 1.1 cm.) most with anthers. Filaments are between 3C and 4B in color sometimes lightly suffused with near 53C. The anthers are moderately small for the class and all open approximately at the same time. Anther color when immature is near 22A on the external part and near 11D on the internal part. Anther color at maturity is near 165B on the external part and near 200A on the internal part. Pollen is moderate and near 23B in color.

FEMALE REPRODUCTIVE ORGANS

Pistils vary in number (average about 35). The styles are moderately even, short in length (about 0.2 to about 0.3 cm.), somewhat thin to average in caliper, and bunched. Stigma color is between 11B and 14D. Style color is near 4D often moderately suffused with near 60A. Ovaries are usually all enclosed in the calyx. The ovaries are of small size and between 158B and 158C in color.

Hips are of somewhat short to average length (about 1.3 to about 2.3 cm.), urn-shaped to moderately rounded in form, and between 34A and 42B in color when ripe. The hip surface is smooth with thick fleshy walls. The sepals are fugacious, and usually straight in shape.

The seeds are irregularly rounded, smooth in texture, approximately 8 to about 13 per hip, about 0.5 to about 0.6 cm. in diameter at the widest point and between 164D and 165D in color.

FOLIAGE

The compound leaves are usually comprised of three to nine leaflets and are borne abundantly. The seven-leaflet leaves are about 11.4 to about 16.2 cm. in length and about 9.2 to about 14.2 cm. in width at the widest point, moderately crisp to somewhat leathery in texture on both sides, and glossy in finish on the upper side and semi-glossy in finish on the under side. The leaves have a pinnate venation pattern. The terminal leaflets are about 5.1 to about 7.7 cm. in length and about 3.0 to about 4.3 cm. in width at the widest point, shaped oval with acute apices and rounded bases. Their margins are usually simply serrate.

The upper surface color of the mature leaf is between 139A and 137B. The under surface color of the mature leaf is between 137C and 138B. The under and upper colors of the leaf veins on the mature leaf are similar in coloration to the upper and under surfaces colors of the mature leaf. The upper surface color of the young leaf is between 137B and 137C, often moderately suffused with near 187B. The under surface color of the young leaf is between 138B and 138A, sometimes moderately suffused with near 187B. The under and upper colors of the leaf veins on the young leaf are similar in coloration to the upper and under surfaces colors of the young leaf.

The rachis is moderately heavy in caliper and rough. The upper side is shallowly grooved with few hairs and some stipitate glands on the edges of the grooves. The under side of the rachis is rough with some stipitate glands and few small prickles. The rachis color is near 146D on the under side and near 137B on the upper side, often heavily suffused on the young leaves with between 187B and 187A.

The stipules are about 1.4 to about 3.1 cm. in length and moderately wide (about 0.5 to about 0.9 cm.) with long straight points that usually turn out at an angle of more than 45 degrees and sometimes recurve toward the stem. The under and upper surface color of the stipule is between 137A and 137B. The upper and under surfaces of the stipules are smooth in texture.

The petiole is moderately heavy in caliper and rough. The upper side is shallowly grooved with few hairs and some stipitate glands on the edges of the grooves. The under side of the petiole is rough with some stipitate glands and few small prickles. The petiole is about 0.4 to about 1.4 cm. in length and about 0.15 to about 0.2 cm in width at the widest point. The petiole color is near 146D on the under side and near 137B on the upper side, often heavily suffused on the young leaves with between 187B and 187A.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has an upright moderately spreading medium height growing habit (about 130 to about 180 cm. in height and about 120 to about 160 cm. spread at the widest point), with moderately full branching. It displays vigorous growth and the canes are of somewhat light to medium caliper for the class (about 1.2 to about 2.2 cm. in diameter at the widest point).

The color of the major stems is between 146A and 146B. The major stems are rough in texture and they bear many large prickles that are about 0.6 to about 1.0 cm. in length. The large prickles are angled moderately to somewhat hooked downward with a long narrow oval base; prickle color is between 177B and 165A often moderately suffused with between 201C and 201D. The major stem bears many small prickles of similar shape and coloration.

The color of the branches is between 137B and 137C. The branches are rough in texture and they bear some large prickles which are of similar size and shape to the large prickles on the major stems; prickle color is between 166C and 164A. The branches bear several small prickles of similar shape and coloration.

The color of the new shoots is between 137C and 146B sometimes lightly suffused with between 187A and 187B. The new shoots are rough in texture and they bear some large prickles which are of similar size and shape to the large prickles on the major stems; prickle color is between 152B and 146C sometimes moderately suffused with between 187C and 187D. The shoots bear several small prickles of similar shape and coloration.

I claim:

1. A new and distinct Floribunda rose plant of the variety substantially as described and illustrated herein.

* * * * *

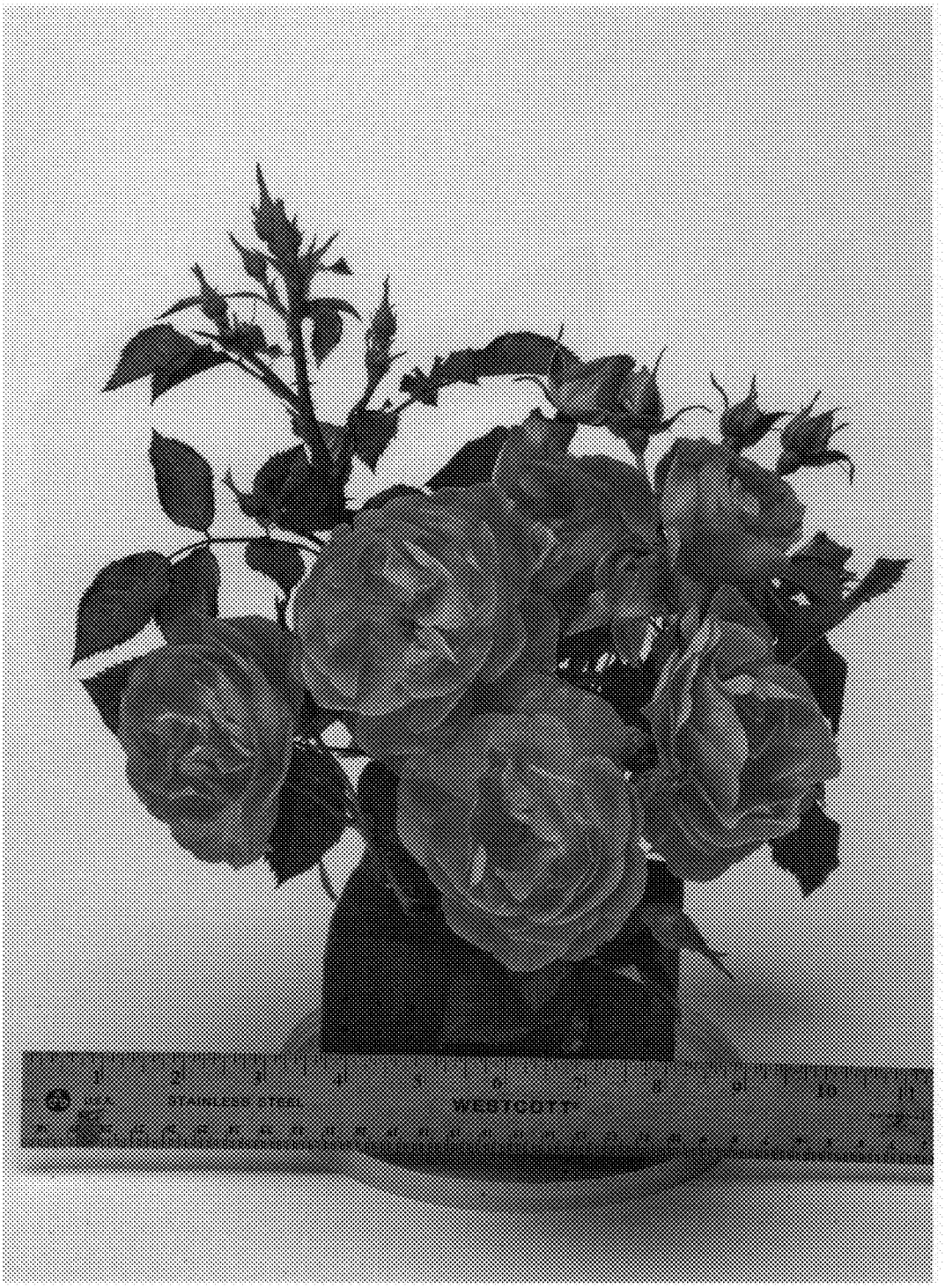
STAINLESS STEEL
WEBTCETT